United States Patent
Hu et al.

(10) Patent No.: US 9,566,040 B2
(45) Date of Patent: Feb. 14, 2017

(54) AUTOMATIC COLLIMATOR ADJUSTMENT DEVICE WITH DEPTH CAMERA AND METHOD FOR MEDICAL TREATMENT EQUIPMENT

(71) Applicant: SWISSRAY ASIA HEALTHCARE CO., LTD., Taipei (TW)

(72) Inventors: Chi Min Hu, Taipei (TW); Jian Chen Guo, Taipei (TW)

(73) Assignee: Swissray Asia Healthcare Co., Ltd., Taipei (TW)

( * ) Notice: Subject to any disclaimer, the term of this patent is extended or adjusted under 35 U.S.C. 154(b) by 215 days.

(21) Appl. No.: 14/339,567

(22) Filed: Jul. 24, 2014

(65) Prior Publication Data

US 2015/0327821 A1 Nov. 19, 2015

(30) Foreign Application Priority Data

May 14, 2014 (TW) ................ 103116932 A
May 14, 2014 (TW) ................ 103116933 A (51) Int. Cl.
| | |
|---|---|
| *A61B 6/00* | (2006.01) |
| *G21K 1/04* | (2006.01) |
| *A61B 6/03* | (2006.01) |
| *G06K 9/20* | (2006.01) |
| *G06T 7/00* | (2006.01) |
| *A61B 6/08* | (2006.01) |

(Continued)

(52) U.S. Cl.
CPC ............. *A61B 6/544* (2013.01); *A61B 5/0077* (2013.01); *A61B 6/035* (2013.01); *A61B 6/06* (2013.01); *A61B 6/08* (2013.01); *A61B 6/46* (2013.01); *A61B 6/5205* (2013.01); *A61B 6/54* (2013.01); *A61B 6/542* (2013.01); *A61B 6/545* (2013.01); *G06K 9/2081* (2013.01); *G06T 7/0065* (2013.01); *G21K 1/04* (2013.01); *G21K 1/046* (2013.01); *G06T 2207/10028* (2013.01); *G06T 2207/20104* (2013.01); *G06T 2207/30196* (2013.01); *G06T 2210/41* (2013.01)

(58) Field of Classification Search
CPC ............... A61B 6/06; A61B 6/08; A61B 6/54; A61B 6/541; A61B 6/542; A61B 6/544; A61B 6/545; G21K 1/04; G21K 1/046
USPC ................... 378/150, 151, 165, 166
See application file for complete search history.

(56) References Cited

U.S. PATENT DOCUMENTS

| | | | | |
|---|---|---|---|---|
| 4,991,189 A | * | 2/1991 | Boomgaarden | A61B 6/06 378/151 |
| 5,260,984 A | * | 11/1993 | Horbaschek | H05G 1/64 378/147 |

(Continued)

*Primary Examiner* — Allen C. Ho
(74) *Attorney, Agent, or Firm* — Rosenberg, Klein & Lee (57) ABSTRACT

An automatic collimator adjustment device and method for medical treatment equipment are disclosed. The medical treatment equipment includes an automatic collimator adjustment device, which includes a processor unit, a depth camera, and a collimator control device. The processor unit receives an instant image pixel depth signal acquired by the depth camera to compare with a predetermined image pixel depth signal of a predetermined human body portion of a target human body in order to generate at least one collimator adjustment signal to the collimator control device, so that the collimator control device controls the collimator to adjust the X-ray beam to align with the predetermined human body portion of the target human body.

14 Claims, 7 Drawing Sheets

(51) Int. Cl.
*A61B 6/06* (2006.01)
*A61B 5/00* (2006.01)

(56) References Cited

U.S. PATENT DOCUMENTS

| | | | | |
|---|---|---|---|---|
| 5,287,396 A * | 2/1994 | Stegehuis | ............... | A61B 6/06 378/151 |
| 5,299,250 A * | 3/1994 | Styrnol | ............... | G01T 1/2985 378/151 |
| 5,377,252 A * | 12/1994 | Liebetruth | ............ | A61B 6/032 378/147 |
| 5,394,455 A * | 2/1995 | Roeck | ................... | A61B 6/464 348/E5.086 |
| 5,412,704 A * | 5/1995 | Horbaschek | ............ | A61B 6/06 378/151 |
| 5,844,962 A * | 12/1998 | Kunert | .................... | H05G 1/26 378/150 |
| 6,055,295 A * | 4/2000 | Murthy | .................... | A61B 6/06 378/145 |
| 6,259,767 B1 * | 7/2001 | Neumann | ............... | A61B 6/06 378/110 |
| 6,393,100 B1 * | 5/2002 | Leeds | ...................... | A61B 6/06 378/147 |
| 6,501,828 B1 * | 12/2002 | Popescu | .................. | A61B 6/06 378/145 |
| 6,507,642 B2 * | 1/2003 | Fujishige | ................ | A61B 6/06 378/150 |
| 6,647,092 B2 * | 11/2003 | Eberhard | ................ | G21K 1/04 378/150 |
| 6,711,236 B2 * | 3/2004 | Izuhara | .................. | A61B 6/035 250/505.1 |
| 6,942,385 B2 * | 9/2005 | Fadler | ..................... | A61B 6/08 378/205 |
| 6,990,175 B2 * | 1/2006 | Nakashima | ............ | A61B 6/032 378/101 |
| 6,999,551 B2 * | 2/2006 | Bressel | ................... | A61B 6/032 378/151 |
| 7,077,568 B2 * | 7/2006 | Hornegger | .............. | A61B 6/06 378/205 |
| 7,113,569 B2 * | 9/2006 | Okumura | ............. | A61B 6/032 378/150 |
| 7,120,231 B2 * | 10/2006 | Spahn | ..................... | A61B 6/06 250/515.1 |
| 7,170,975 B2 * | 1/2007 | Distler | ................... | A61B 6/032 378/147 |
| 7,194,061 B2 * | 3/2007 | Fujita | ..................... | A61B 6/032 378/150 |
| 7,263,171 B2 * | 8/2007 | Zhang | ...................... | G21K 1/04 250/505.1 |
| 7,372,945 B2 * | 5/2008 | Geisser | ................... | G21K 1/04 378/146 |
| 7,409,034 B2 * | 8/2008 | Gohno | ................... | A61B 6/032 378/15 |
| 7,488,108 B2 * | 2/2009 | Pommi | .................. | A61B 6/469 378/205 |
| 7,489,765 B2 * | 2/2009 | Yi | ............................ | G21K 1/04 378/145 |
| 7,494,276 B2 * | 2/2009 | Borgmann | ............... | A61B 6/08 378/162 |
| 7,526,065 B2 * | 4/2009 | Hardesty | ................ | A61B 6/542 378/145 |
| 7,620,147 B2 * | 11/2009 | Gertner | .................. | A61N 5/10 378/145 |
| 7,706,500 B2 * | 4/2010 | Kondo | ................... | A61B 6/032 378/15 |
| 8,009,794 B2 * | 8/2011 | Partain | .................. | A61B 6/032 378/150 |
| 8,094,775 B2 * | 1/2012 | Noshi | .................... | A61B 6/032 378/15 |
| 8,213,568 B2 * | 7/2012 | Heuscher | ................ | A61B 6/06 378/15 |
| 8,213,569 B2 * | 7/2012 | Zaiki | ...................... | A61B 6/035 378/147 |
| 8,467,495 B2 * | 6/2013 | Okada | .................... | A61B 6/022 378/151 |
| 8,503,607 B2 * | 8/2013 | Takasaki | ................. | A61B 6/08 378/62 |
| 8,873,708 B2 * | 10/2014 | Sugiyama | ............... | A61B 6/06 378/151 |
| 8,956,044 B2 * | 2/2015 | Hummel | ................. | A61B 6/06 378/150 |
| 9,008,269 B2 * | 4/2015 | Wang | ...................... | A61B 6/52 378/146 |
| 9,149,247 B2 * | 10/2015 | Lee | ........................ | A61B 6/4452 |
| 9,348,337 B2 * | 5/2016 | Chen | ....................... | A61B 6/102 |
| 9,462,985 B2 * | 10/2016 | Hu | ........................... | A61B 6/5205 |
| 2015/0327830 A1 * | 11/2015 | Hu | ........................... | A61B 6/06 378/8 |

* cited by examiner

AUTOMATIC COLLIMATOR ADJUSTMENT DEVICE WITH DEPTH CAMERA AND METHOD FOR MEDICAL TREATMENT EQUIPMENT

BACKGROUND OF THE INVENTION

1. Field of the Invention

The present invention relates to a device and a method for controlling a collimator of medical treatment equipment, and in particular to an automatic collimator adjustment device combined with the medical treatment equipment to control the operation of a collimator of the medical treatment equipment for adjusting an X-ray beam projecting to a predetermined body portion of a target human body.

2. the Related Arts

Currently, medical examination often applies X-ray beam imaging. The X-ray beam imaging generally uses and adjusts shielding plates to determine the size of a radiation area in order to control the radiation range and reduce dosage absorption of unnecessary portions. In a conventional design, an operator needs to manually or semi-automatically adjust the shielding plates and the portion and the range of radiation are selected through adjustments made in upward/downward and leftward/rightward.

Heretofore, a radiographer or medical personnel has to make determination through visual inspection and manually adjust the shielding plates. This causes an issue of being not easy to carry out the operation. Further, during the operation that a radiographer or medical personnel makes the adjustment, the size of the radiation area, and the radiation zone may readily occur due to difference in respect of personal experience, expertise, habit, and personal emotional issues. For example, an X-ray photograph that is incorrect in respect of the radiation range or radiation area may lead to incorrect reading of visual inspection by a treating operator and may even lead to incorrect diagnosis. Further, the chance that a patient has to take the examination once more due to the error of the operation may often be thus increased. In addition, the time that a radiographer needs to spend in photographing may be increased due to the inconvenience of manual adjustment of the shielding plates.

It is thus a challenge to the industry to overcome the above-discussed problems and issues.

SUMMARY OF THE INVENTION

To overcome the above-discussed problems and issues, an object of the present invention is to provide an automatic collimator adjustment system for medical treatment equipment, in which identification is made with comparing an instant image pixel depth signal with a human body portion image pixel depth signal to provide at least one collimator adjustment signal to control a collimator of the medical treatment equipment thereby achieving automatic adjustment of an X-ray beam aligning with a predetermined human body portion of a target human body.

The technical solution that the present invention adopts to achieve the above object is that an automatic collimator adjustment device is included in medical treatment equipment and comprises a processor unit, a depth camera, and a collimator control device. The processor unit receives an instant image pixel depth signal acquired by the depth camera to compare with a predetermined image pixel depth signal of a predetermined human body portion in order to generate at least one collimator adjustment signal that is transmitted to the collimator control device, whereby the collimator control device controls the collimator to adjust the X-ray beam to align with the predetermined human body portion of a target human body.

The collimator control device comprises a first direction drive motor, which drives a pair of first-direction arranged shielding plates of the collimator to move in a first direction; and a second direction drive motor, which drives a pair of second-direction arranged shielding plates of the collimator to move in a second direction.

The collimator control device further comprises a rotation drive motor, which drives the collimator to rotate about a rotation axial direction.

The processor unit is further connected to an image capture device to capture at least one instant image of the target human body.

The processor unit is further connected to a display device to display the instant image and the instant image pixel depth signal of the target human body. The predetermined image pixel depth signal may be pre-stored in an image data storage device or can be alternatively generated by an operator operating a touch display device or a coordinate position marking device.

The efficacy is that with the above technical solution of the present invention, medical personnel, when operating a collimator included in an X-ray medical treatment equipment, may use the automatic collimator adjustment device of the present invention to automatically detect a predetermined human body portion of a target human body, whereby errors caused by lacking of experience of a radiographer or poor habit thereof can be reduced and the inconvenience and time required for manual adjustment of a shielding plates may be greatly reduced.

BRIEF DESCRIPTION OF THE DRAWINGS

The present invention will be apparent to those skilled in the art by reading the following description of preferred embodiments of the present invention, with reference to the attached drawings, in which.

DETAILED DESCRIPTION OF THE PREFERRED EMBODIMENTS

Figure 1:
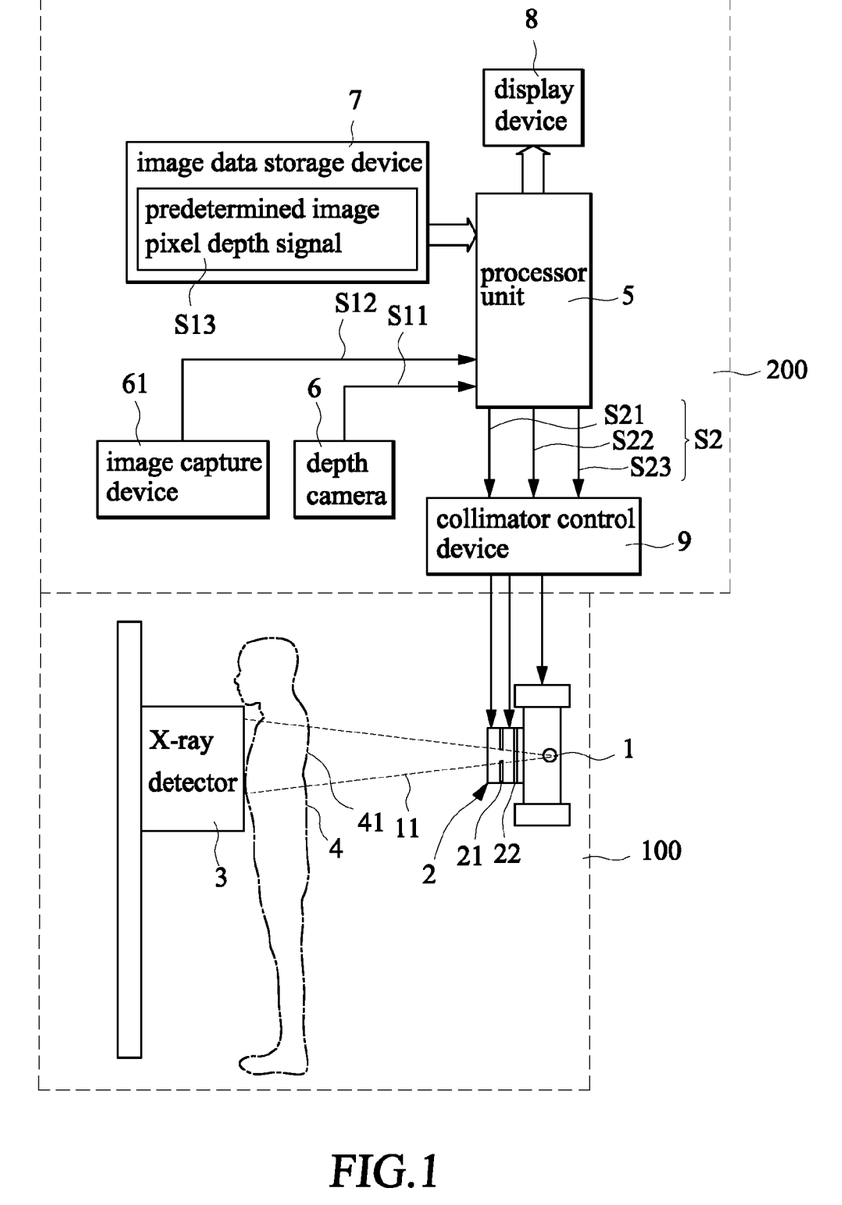
FIG. 1 is a schematic view of a circuit system of a first embodiment according to the present invention.

With reference to the drawings and in particular to FIG. 1, a first embodiment is illustrated, in which medical treatment equipment 100 is arranged to include an X-ray source generator 1, a collimator 2, and an X-ray detector 3. The X-ray source generator 1 is coupled to the collimator 2. The X-ray detector 3 is arranged at a position that is spaced from the X-ray source generator 1 by a predetermined distance.

The X-ray source generator 1 emits an X-ray beam 11, which, after passing through shielding plates 21 and a filter 22 arranged in the collimator 2, is projected to a target human body 4 and is detected by the X-ray detector 3.

In the present invention, an automatic collimator adjustment device 200 is combined with and coupled to the medical treatment equipment 100 to control the operation of the collimator 2 of the medical treatment equipment 100 and thus controlling the X-ray beam 11 that is projected to a predetermined human body portion 41 of the target human body 4.

The automatic collimator adjustment device 200 according to the present invention comprises a processor unit 5, a depth camera 6, an image data storage device 7, a display device 8, and a collimator control device 9.

The depth camera 6 is set at a position corresponding to the target human body 4 in order to acquire at least one instant image pixel depth signal S11 of the target human body 4. The depth camera 6 is connected to the processor unit 5 to transmit the acquired instant image pixel depth signal S11 to the processor unit 5.

In addition to the depth camera 6, an image capture device 61 may be provided and connected to the processor unit 5 in order to acquire at least one instant image S12 of the target human body 4 and transmit the instant image S12 to the processor unit 5.

The image data storage device 7 is connected to the processor unit 5 and stores therein at least one predetermined image pixel depth signal S13 of the predetermined human body portion 41.

The display device 8 is connected to the processor unit 5 to display the instant image pixel depth signal S11 of the target human body 4 acquired by the depth camera 6 and the instant image S12 of the target human body 4 acquired by the image capture device 61.

The collimator control device 9 is connected to the processor unit 5 and the collimator 2. The collimator control device 9, which is under the control of the processor unit 5, controls the operation of the collimator 2.

To carry out an operation of automatic adjustment of the collimator 2, the processor unit 5 compares the instant image pixel depth signal S11 received thereby with the predetermined image pixel depth signal S13 stored in the image data storage device 7. According to the result of comparison, if the instant image pixel depth signal S11 and the predetermined image pixel depth signal S13 are different, the processor unit 5 generates, according to the difference between the instant image pixel depth signal S11 and the predetermined image pixel depth signal S13, at least one collimator adjustment signal S2 that is transmitted to the collimator control device 9, so that the collimator control device 9 may follow the collimator adjustment signal S2 to control the operation of the collimator 2.

Figure 2:
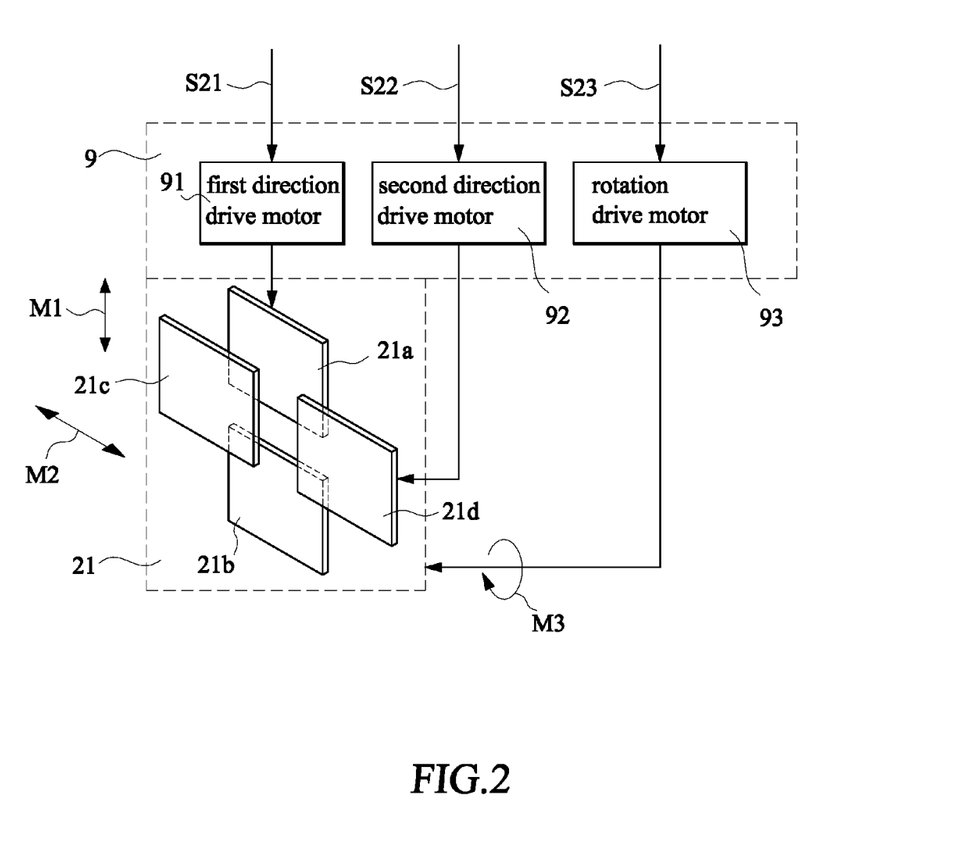
FIG. 2 is a schematic view showing a detailed circuit diagram of a collimator control device and a collimator of FIG. 1.

Also referring to FIG. 2, in a preferred embodiment of the present invention, the collimator adjustment signal S2 generated by the processor unit 5 comprises a first direction drive signal S21, a second direction drive signal S22, and a rotation drive signal S23.

The collimator control device 9 comprises a first direction drive motor 91, a second direction drive motor 92, and a rotation drive motor 93. The first direction drive motor 91 functions to drive a pair of first-direction arranged shielding plates 21a, 21b of the collimator 2 to move in a first direction M1. Thus, the first direction drive motor 91, when receiving the first direction drive signal S21 transmitted from the processor unit 5, drives the first-direction arranged shielding plates 21a, 21b of the collimator 2 to move in the first direction M1. In an actual operation, the first-direction arranged shielding plates 21a, 21b are controlled by the first direction drive signal S21 to synchronously move in the same direction or in opposite directions along conventional components, such as a rail or rollers.

The second direction drive motor 92 functions to drive a pair of second-direction arranged shielding plates 21c, 21d of the collimator 2 to move in a second direction M2. Then, the second direction drive motor 92, when receiving the second direction drive signal S22 from the processor unit 5, drives the second-direction arranged shielding plates 21c, 21d of the collimator 2 to move in the second direction M2. In an actual operation, the second-direction arranged shielding plates 21c, 21d are controlled by the second direction drive signal S22 to synchronously move in the same direction or in opposite directions along conventional components, such as a rail or rollers.

The rotation drive motor 93 functions to drive the collimator 2 to rotate about a rotation axial direction M3. Thus, the rotation drive motor 93, when receiving the rotation drive signal 323 transmitted from the processor unit 5, drives the collimator 2 to rotate about the rotation axial direction M3.

With the above-described control operations, control of the collimator 2 can be achieved for the purpose of adjusting the X-ray beam 11 to align with the predetermined human body portion 41 of the target human body 4.

Figure 3:
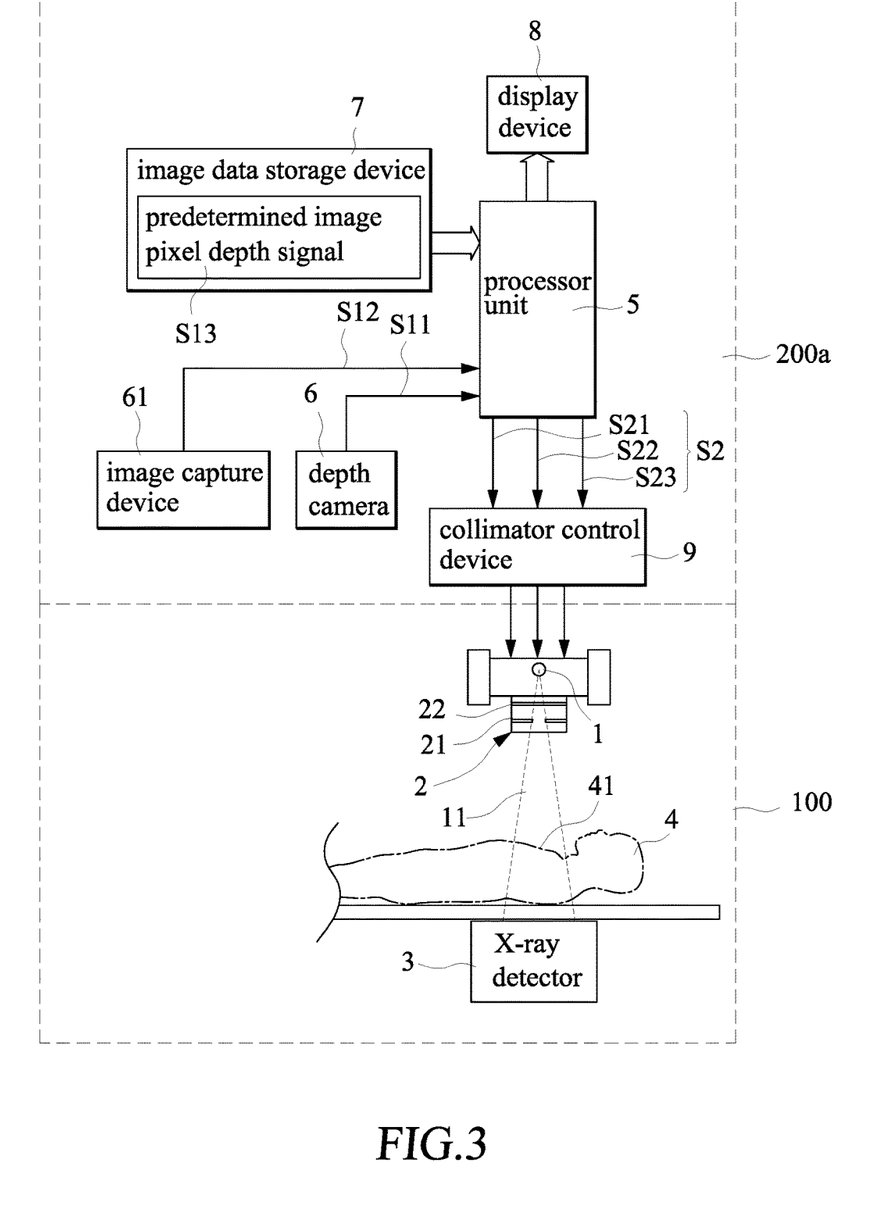
FIG. 3 is a schematic view of a circuit system of a second embodiment according to the present invention.

FIG. 3 is a schematic view showing a circuit system according to a second embodiment of the present invention. The constituent components of the instant embodiment are substantially identical to those of the first embodiment and identical components are designated with the same reference numerals for consistency. In the instant embodiment, the medical treatment equipment 100 similarly comprises an X-ray source generator 1, a collimator 2, and an X-ray detector 3. However, the collimator 2 and the X-ray detector 3 are arranged in a vertical direction and thus, the target human body 4 is allowed to lie horizontally on a treatment bed. The automatic collimator adjustment device 200a of the present invention controls the operation of the collimator 2 of the medical treatment equipment 100 in a similar way so as to achieve adjustment of the X-ray beam 11 projecting to the predetermined human body portion 41 of the target human body 4.

Figure 4:
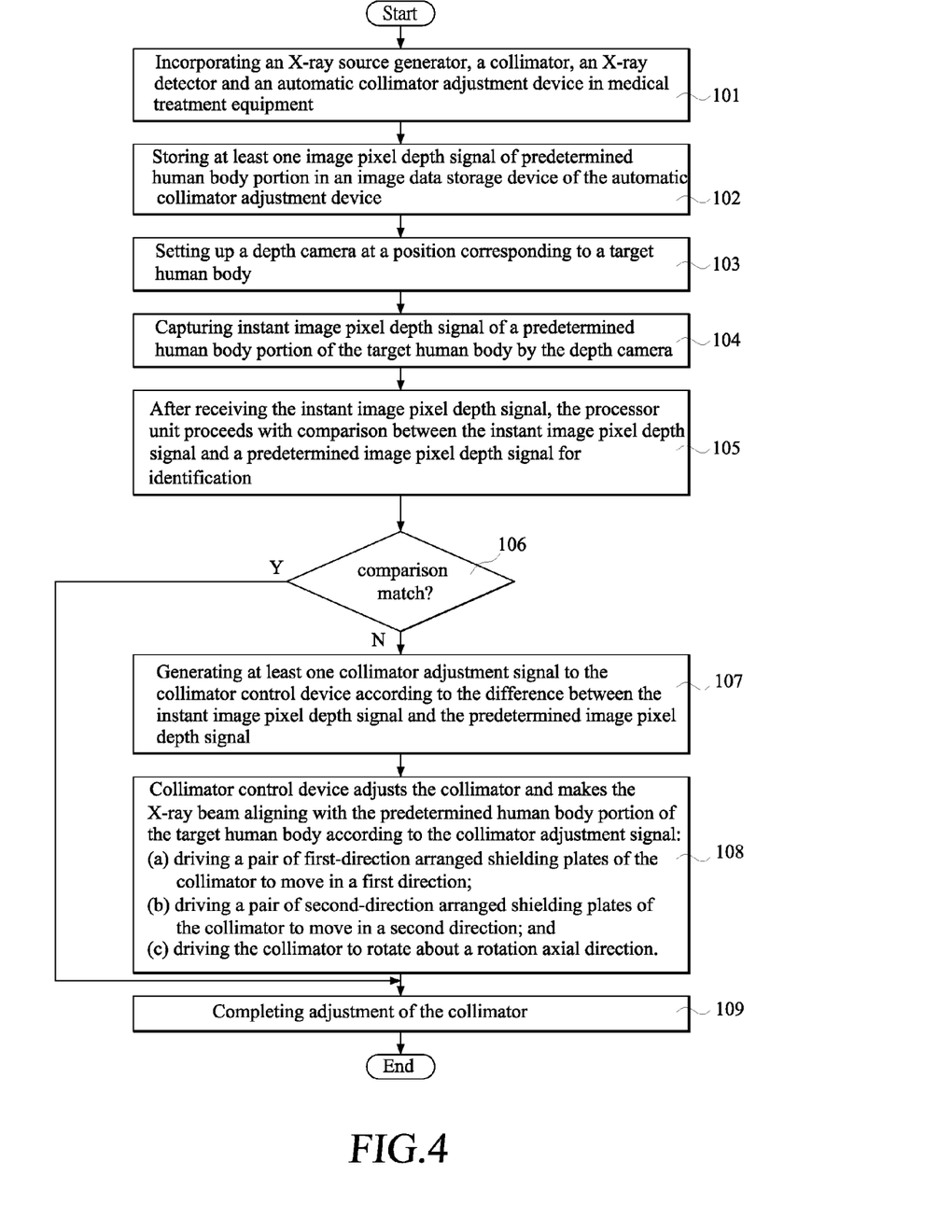
FIG. 4 is a flow chart for the first and second embodiments of the present invention.

FIG. 4 shows a flow chart for the first and second embodiments of the present invention. Reference is also made to FIGS. 1 and 2 for illustration of the flow of the operation of the present invention. Firstly, an X-ray source generator 1, a collimator 2, an X-ray detector 3, and an automatic collimator adjustment device 200 and 200a according to the present invention are arranged in medical treatment equipment 100 (Step 101). At least one predetermined image pixel depth signal S13 is established and stored in the image data storage device 7 of the automatic collimator adjustment device 200 and 200a of the present invention (Step 102). A depth camera 6 is set up at a position corresponding to a target human body 4 (Step 103).

When a target human body 4 is set at a correct position corresponding to the X-ray source generator 1, the depth camera 6 is operated to capture at least one instant image pixel depth signal S11 of a predetermined human body portion 41 of the target human body 4 (Step 104) and the instant image pixel depth signal S11 is transmitted to the processor unit 5.

After receiving the instant image pixel depth signal S11, the processor unit 5 proceeds with comparison between the instant image pixel depth signal S11 and the predetermined image pixel depth signal S13 stored in the image data storage device 7 for identification (Step 105).

If the result of comparison does not match (Step 106), indicating the instant image pixel depth signal S11 and the predetermined image pixel depth signal S13 are different, the processor unit 5 generates, according to the difference between the instant image pixel depth signal S11 and the predetermined image pixel depth signal S13, at least one collimator adjustment signal S2 that is transmitted to the collimator control device 9 (Step 107), so that the collimator control device 9 follows the collimator adjustment signal S2 to adjust the collimator 2 and make the X-ray beam 11 aligning with the predetermined human body portion 41 of the target human body 4 (Step 108) to finally complete the control of adjustment of the collimator 2 (Step 109).

In a preferred embodiment of the present invention, the collimator adjustment signal 32 comprises a first direction drive signal S21, a second direction drive signal S22, and a rotation drive signal S23 and the operation thereof comprises:

(a) driving a pair of first-direction arranged shielding plates 21a, 21b of the collimator 2 to move in a first direction M1;

(b) driving a pair of second-direction arranged shielding plates 21c, 21d of the collimator 2 to move in a second direction M2; and (c) driving the collimator 2 to rotate about a rotation axial direction M3.

Figure 5:
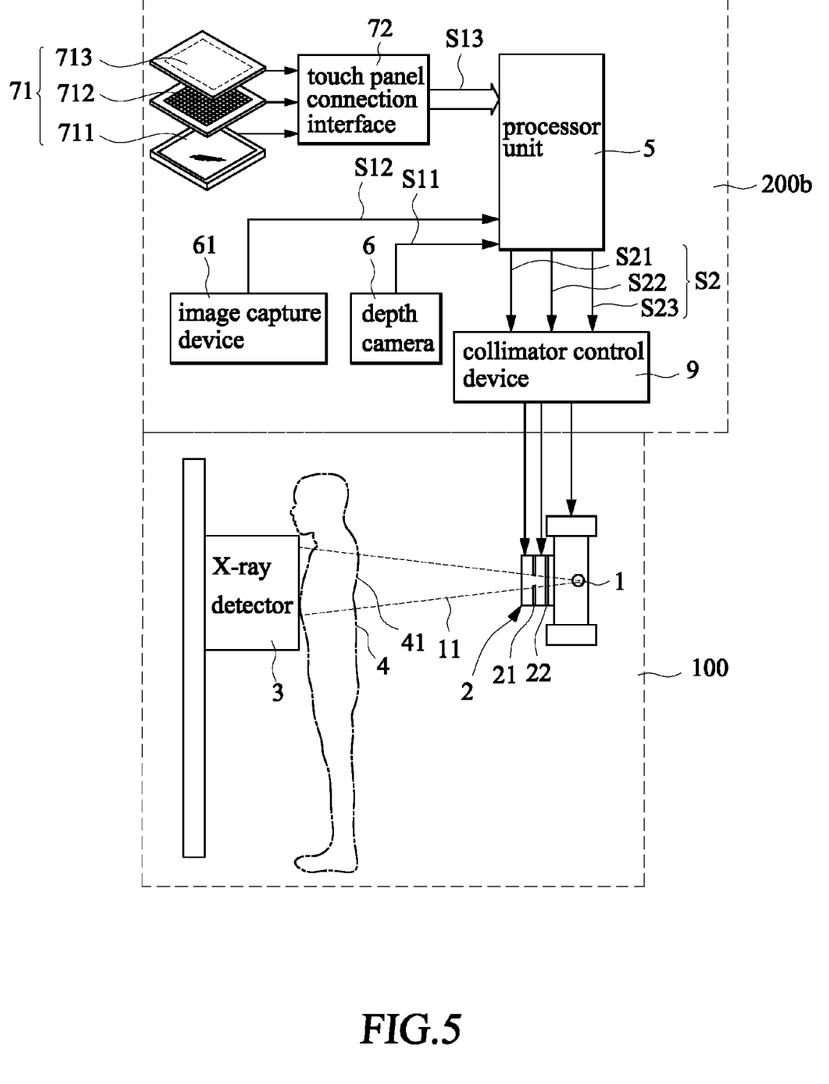
FIG. 5 is a schematic view of a circuit system of a third embodiment according to the present invention.

FIG. 5 is a schematic view showing a circuit system of a third embodiment according to the present invention. The constituent components of the instant embodiment are substantially identical to those of the first embodiment shown in FIG. 1 and identical components are designated with the same reference numerals for consistency. The difference is that the automatic collimator adjustment device 200b includes a touch display device 71 which is connected via a touch panel connection interface 72 to the processor unit 5. The touch display device 71 comprises a display panel 711, a touch panel 712, and a protection surface 713.

Figure 6:
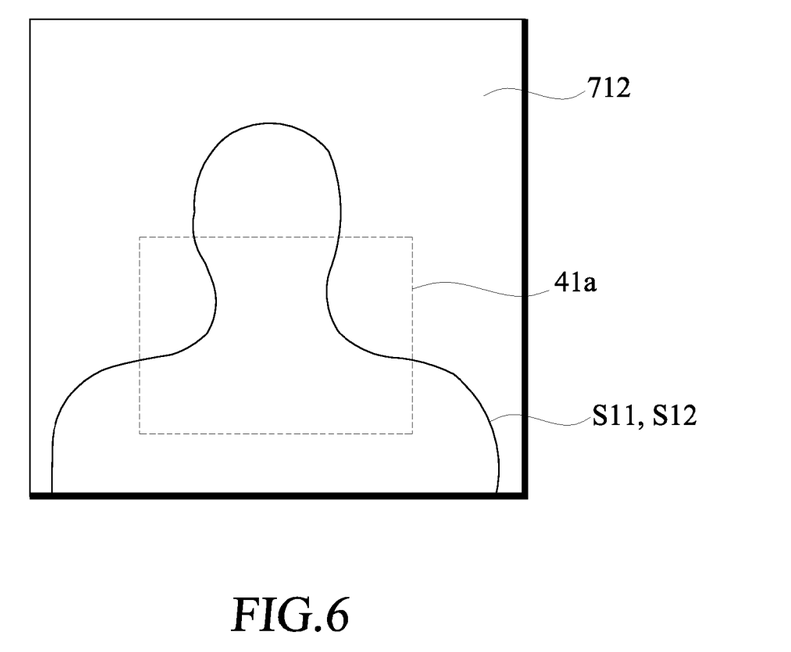
FIG. 6 illustrates in the embodiment of FIG. 5, an operator is allowed to select among candidate human body portions shown in an image displayed on a display panel for performance of X-ray radiation.

An operator may operate the touch panel 712 via an instant image pixel depth signal S11 or an instant image S12 displayed on the display panel 711 to pick up a selected human body area 41a to which X-ray beam 11 is to irradiate (as shown in FIG. 6) and the touch panel connection interface 72 forwards a predetermined image pixel depth signal S13 of the predetermined human body portion 41 to the processor unit 5.

The processor unit 5 compares the instant image pixel depth signal S11 and the predetermined image pixel depth signal S13 of the predetermined human body portion 41. According to the result of comparison, if the instant image pixel depth signal S11 and the predetermined image pixel depth signal S13 are different, the processor unit 5 generates, according to the difference between the instant image pixel depth signal S11 and the predetermined image pixel depth signal S13, at least one collimator adjustment signal S2 that is transmitted to the collimator control device 9, so that the collimator control device 9 may follow the collimator adjustment signal S2 to control the operation of the collimator 2.

Figure 7:
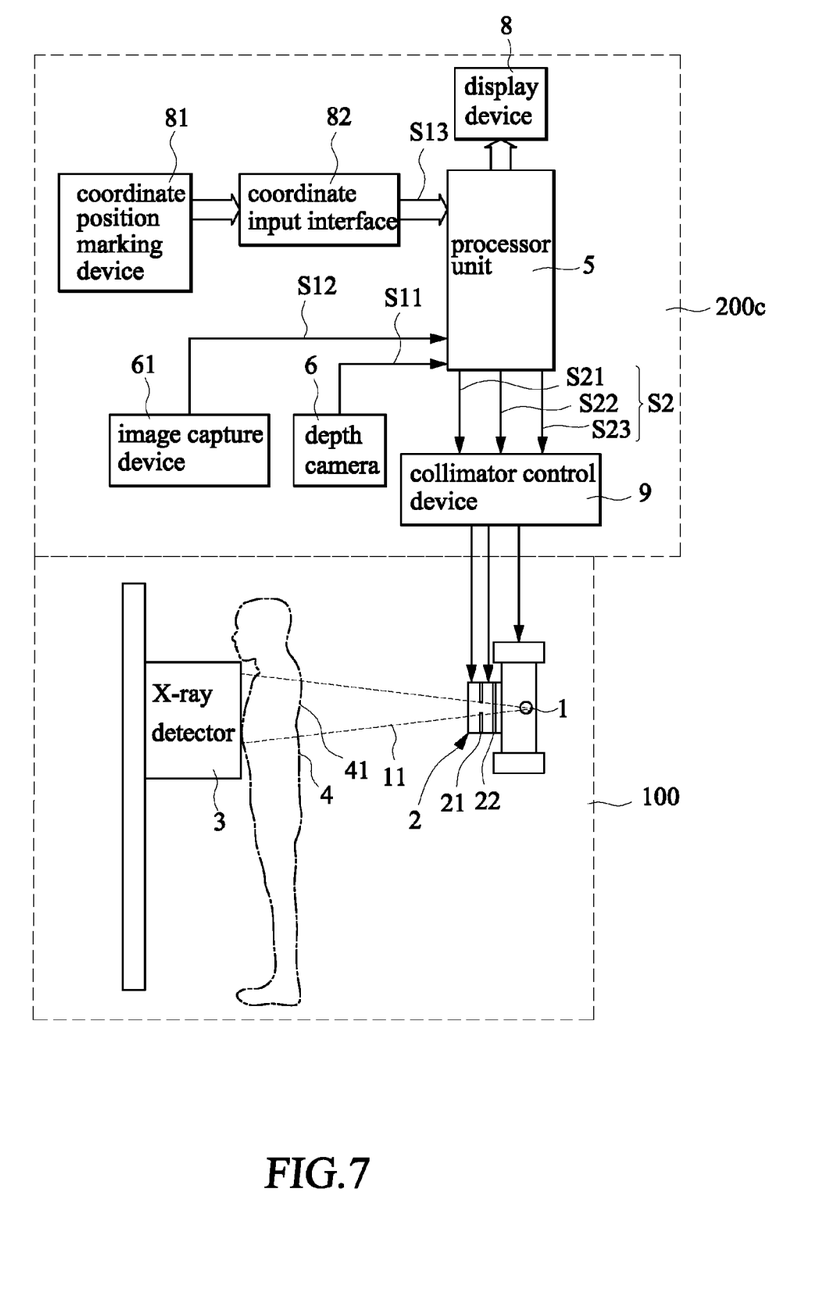
FIG. 7 is a schematic view of a circuit system of a fourth embodiment according to the present invention.

FIG. 7 is a schematic view showing a circuit system of a fourth embodiment according to the present invention. The constituent components of an automatic collimator adjustment device 200c of the instant embodiment are substantially identical to those of the embodiment shown in FIG. 5, the difference being that a coordinate position marking device 81 is connected via a coordinate input interface 82 to the processor unit 5.

An operator may operate the coordinate position marking device 81 via an image pixel depth signal S11 or an instant image S12 displayed on the display device 8 to pick up a selected human body area 41a to which X-ray beam 11 is to irradiate, and the coordinate input interface 82 forwards a predetermined image pixel depth signal S13 of the predetermined human body portion 41 to the processor unit 5.

The processor unit 5 compares the instant image pixel depth signal S11 and the predetermined image pixel depth signal S13 of the predetermined human body portion 41. According to the result of comparison, if the instant image pixel depth signal S11 and the predetermined image pixel depth signal S13 are different, the processor unit 5 generates, according to the difference between the instant image pixel depth signal S11 and the predetermined image pixel depth signal S13 of the predetermined human body portion 41, at least one collimator adjustment signal S2 that is transmitted to the collimator control device 9, so that the collimator control device 9 may follow the collimator adjustment signal S2 to control the operation of the collimator 2.

Although the present invention has been described with reference to the preferred embodiments thereof, it is apparent to those skilled in the art that a variety of modifications and changes may be made without departing from the scope of the present invention which is intended to be defined by the appended claims.

What is claimed is:

1. An automatic collimator adjustment device for a medical treatment equipment, in which the medical treatment equipment includes an X-ray source generator, a collimator, and an X-ray detector, wherein the X-ray source generator projects an X-ray beam to a target human body through the collimator and the X-ray detector detects the X-ray beam, the automatic collimator adjustment device comprising:

a processor unit;

a depth camera, which is connected to the processor unit and is set at a position corresponding to the target human body to acquire at least one instant image pixel depth signal of the target human body; and a collimator control device, which is connected to the processor unit and the collimator, wherein the processor unit receives and compares the at least one instant image pixel depth signal from the depth camera with a predetermined image pixel depth signal of a predetermined human body portion of the target human body to correspondingly generate at least one collimator adjustment signal to the collimator control device, whereby the collimator control device controls the collimator to adjust the X-ray beam aligning with the predetermined human body portion of the target human body.

2. The automatic collimator adjustment device as claimed in claim 1, wherein the collimator control device comprises:

a first direction drive motor, which drives a pair of first-direction arranged shielding plates of the collimator to move in a first direction; and a second direction drive motor, which drives a pair of second-direction arranged shielding plates of the collimator to move in a second direction.

3. The automatic collimator adjustment device as claimed in claim 1, wherein the collimator control device comprises:

a rotation drive motor, which drives the collimator to rotate about a rotation axial direction.

4. The automatic collimator adjustment device as claimed in claim 1, further comprising an image capture device connected to the processor unit.

5. The automatic collimator adjustment device as claimed in claim 1, further comprising a display connected to the processor unit.

6. The automatic collimator adjustment device as claimed in claim 1, further comprising an image data storage device, which is connected to the processor unit and stores therein the predetermined image pixel depth signal of the predetermined human body portion.

7. The automatic collimator adjustment device as claimed in claim 1, comprising a touch display device connected via a touch panel connection interface to the processor unit, the touch display device comprising a touch panel and a display panel;

the touch panel being operated to pick up a selected human body area to generate the predetermined image pixel depth signal of the predetermined human body portion to the processor unit through the touch panel connection interface.

8. The automatic collimator adjustment device as claimed in claim 1, further comprising a coordinate position marking device connected via a coordinate input interface to the processor unit;

the coordinate position marking device being operated to pick up a selected human body area to generate the predetermined image pixel depth signal of the predetermined human body portion to the processor unit through the coordinate input interface.

9. An automatic collimator adjustment method for a medical treatment equipment, in which the medical treatment equipment includes an X-ray source generator, a collimator, an X-ray detector, and an automatic collimator adjustment device, wherein the X-ray source generator projects an X-ray beam to a target human body and the X-ray detector detects the X-ray beam, wherein the automatic collimator adjustment device controls the collimator to adjust the X-ray beam projecting to a predetermined human body portion of the target human body, the method comprising the following steps:

(a) acquiring at least one instant image pixel depth signal of the target human body by a depth camera;

(b) receiving the at least one instant image pixel depth signal and comparing the at least one instant image pixel depth signal with a predetermined image pixel depth signal of the predetermined human body portion;

(c) if the at least one instant image pixel depth signal and the predetermined image pixel depth signal are different, generating, according to a difference between the at least one instant image pixel depth signal and the predetermined image pixel depth signal, at least one collimator adjustment signal to a collimator control device; and (d) receiving the at least one collimator adjustment signal and then adjusting the collimator by the collimator control device to align the X-ray beam with the predetermined human body portion of the target human body.

10. The automatic collimator adjustment method as claimed in claim 9, wherein in step (d), wherein adjusting the collimator by the collimator control device comprises the following steps:

(d1) driving a pair of first-direction arranged shielding plates of the collimator to move in a first direction; and (d2) driving a pair of second-direction arranged shielding plates of the collimator to move in a second direction.

11. The automatic collimator adjustment method as claimed in claim 9, wherein in step (d), wherein adjusting the collimator by the collimator control device comprises the following step:

(d3) driving the collimator to rotate about a rotation axial direction.

12. The automatic collimator adjustment method as claimed in claim 9, further comprising pre-storing the predetermined image pixel depth signal in an image data storage device.

13. The automatic collimator adjustment method as claimed in claim 9, further comprising picking up a selected human body area in a touch display device.

14. The automatic collimator adjustment method as claimed in claim 9, further comprising picking up a selected human body area in a coordinate position marking device.

* * * * *